United States Patent [19]

Holtermann et al.

[11] Patent Number: 4,846,798
[45] Date of Patent: Jul. 11, 1989

[54] TWO PIECE OSTOMY CONNECTION DEVICE

[75] Inventors: Henri Holtermann, Saint-Jean-de-Luz; Claude Hamelin, Ascain, both of France

[73] Assignee: Laboratoires Biotrol, Paris, France

[21] Appl. No.: 113,581

[22] Filed: Oct. 26, 1987

[30] Foreign Application Priority Data

Oct. 31, 1986 [FR] France .................................. 86 15187

[51] Int. Cl.[4] ............................................. A61F 5/44
[52] U.S. Cl. .................................................. 604/339
[58] Field of Search ............................... 604/332–345; 215/332, 331

[56] References Cited

U.S. PATENT DOCUMENTS

| 1,849,522 | 3/1932 | Hammar | 215/331 |
| 3,736,934 | 6/1973 | Hennessy | 604/342 |
| 4,373,641 | 2/1983 | Banich, Sr. et al. | 215/232 |

FOREIGN PATENT DOCUMENTS

| 149391 | 7/1985 | European Pat. Off. | |
| 163979 | 12/1985 | European Pat. Off. | |
| 2121902 | 1/1984 | United Kingdom | 604/332 |
| 2148716 | 6/1985 | United Kingdom | 604/339 |

Primary Examiner—Jerome L. Kruter
Attorney, Agent, or Firm—Bell, Seltzer, Park & Gibson

[57] ABSTRACT

An improved ostomy device is provided having two elements one of which is provided to be fixed about an artifical opening in the body of the user by means of a pressure sensitive adhesive means, a belt or any other similar means, and the other of which includes a collecting pocket for collecting body fluids and/or waste intended to be removably coupled to said first element by screwing means formed on two end pieces, a first one of which is fixed to a shoe forming a cutaneous protector of the peristomial zone and about an opening in said shoe, whereas the second is fixed about an opening in the connecting pocket, said first end piece, which may also be fixed about the outlet of one or more probes or similar which is or are fast therewith, as well as said second end piece is provided with means ensuring sealing of the device during fitting together of the two elements by screwing.

12 Claims, 3 Drawing Sheets

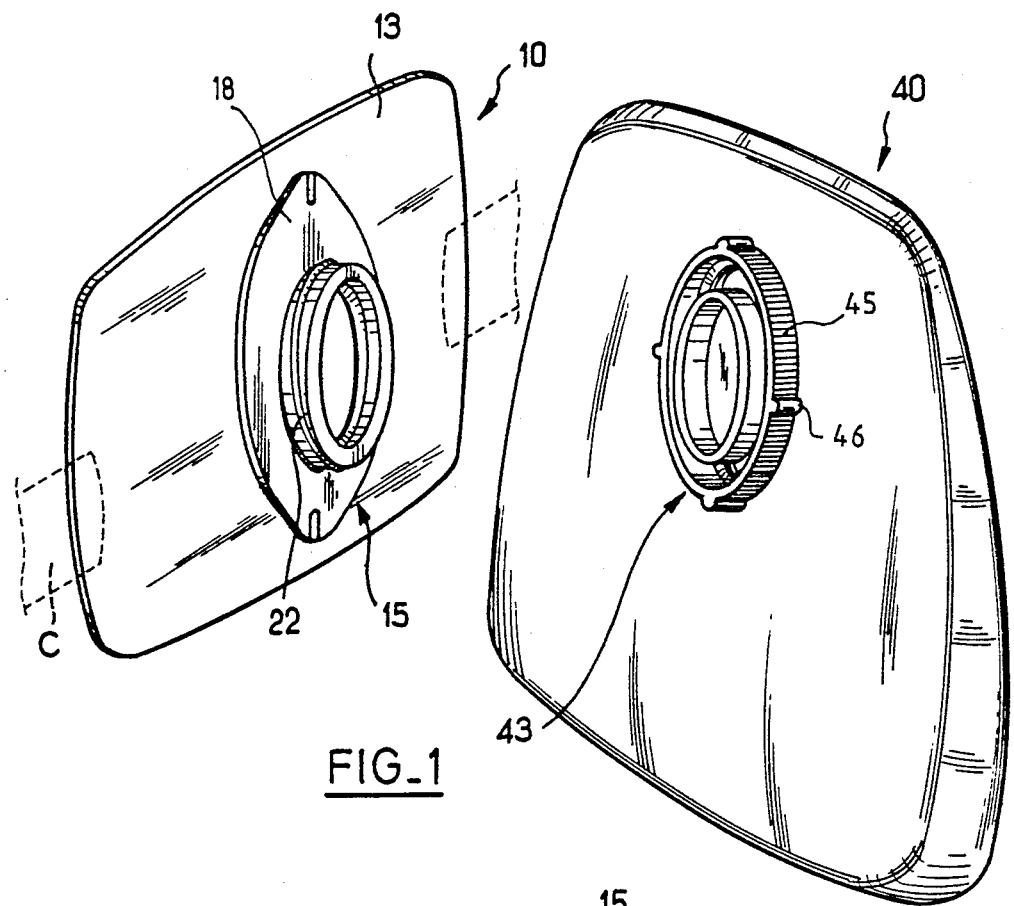
FIG_1
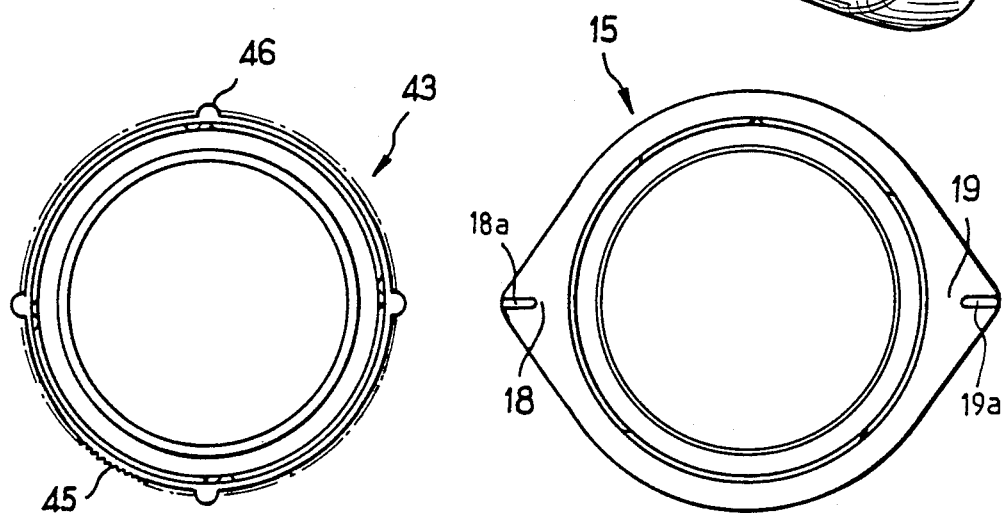
FIG_2    FIG_3

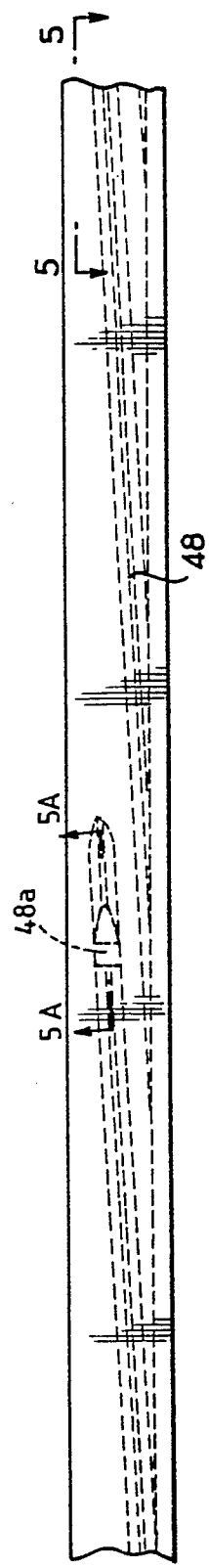
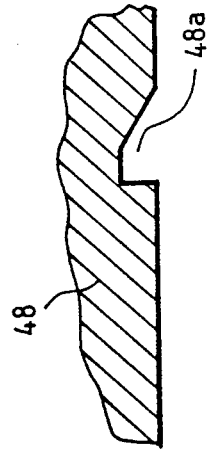
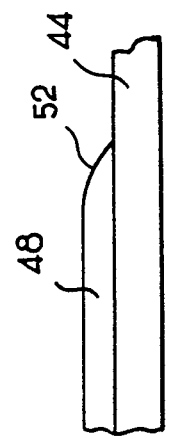
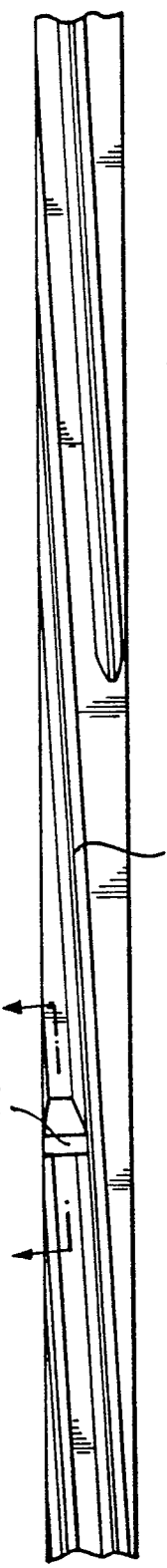

TWO PIECE OSTOMY CONNECTION DEVICE

BACKGROUND OF THE INVENTION

1. Field of the Invention

The invention relates to an improved ostomy device.

It is known that some surgical operations on the gastro-intestinal tract or the urinary apparatus are accompanied in the patient having undergone such operations by the creation of an artifical physiological orifice, with which a body fluid collection means is sometimes associated, such as a collecting probe for urine or similar. The fluids eliminated or, in the case of abdominal ostomy, the body waste is generally collected in a collecting pocket, numerous constructions of which are known.

2. Description of the Prior Art

In some of them, provided for so called two element ostomy devices and described for example in EP-A-O 171 255 or by FR-A No. 2 387 643, the collecting pocket is a disposable bag, or a bag which may be emptied, adapted for being removably fixed to a ring device fixed to the body of the user by an adhesive pad and/or by a belt. The collecting pocket is positioned on a fitting ring or flange fixed to the body of the user, by a snap fit resulting from thrust or pressure which he applies about the ostomy opening so as to cause said ring or flange to cooperate with a sealing fit with a part of conjugate form fixed to the collecting pocket.

In other known devices, the pocket for collecting body waste or fluids is provided with a ring or similar made from a pressure sensitive adhesive material and said pocket is positioned by causing the ring to adhere to a protective means fixed to the body of the user, also under the action of the pressure from the user.

However, since the zone adjacent the ostomy opening is sensitive, generally painful, the application of a pressure only increases the discomfort of the user, so that neither type of device mentioned above is entirely satisfactory. Furthermore, fitting with insufficient pressure does not guarantee sealing of the device, with the extremely disagreeable consequences which result therefrom for the user. These drawbacks, also mentioned in the EP-A-O 163 979 are overcome, in his document, by proposing several bayonet systems or a device in which a collecting pocket is connected to a threaded hub, so that pressure is not used for removably fitting the pocket to the conjugate element of the device fixed to the body of the user. In this device, as well as in that described in GB-A-1 021 145, the indispensable sealing of the device is obtained by cooperation of the hub and the ring so that, if it is sufficient, the device is necessarily formed with close tolerances and therefore the pocket is difficult to position and to remove. Moreover, in the construction described in the British patent, the pocket is not provided integral with the ring, but must be fixed thereto by the user, which is not always without drawbacks.

Thus, consequently, a general purpose of the invention is to provide an improved ostomy device which is simpler and more reliable to use than the known devices.

A futher aim of the invention is to provide such a device which finds an application not only in abdominal ostomy cases but also for ostomies of the urinary system in which a semipermanent system is sometimes used, that is to say in which the pocket or bag for collecting urine is provided with a means for eliminating its contents, so that the device is not renewed at each urination but is kept by the user for one or more days.

SUMMARY OF THE INVENTION

The ostomy device of the invention, having two elements one of which is provided to be fixed about an artificial opening in the body of the user by means of a pressure sensitive adhesive means, a belt or any other similar means, and the other of which includes a collecting pocket for collecting body fluids and/or waste intended to be removably coupled to the first element by screwing means formed on two tubular end pieces, a first one of which is fixed to a pad forming a cutaneous protector of the peristomial zone and about an opening in said pad whereas the second is fixed about an opening in the connecting pocket, is characterized in that said first end piece, which may also be fixed about the outlet of one or more probes or similar which is or are fast therewith, as well as said second end piece are provided with means ensuring sealing of the device during fitting together of the two elements by screwing.

In a preferred embodiment, said sealing elements are formed by an annular lip with triangular cross section coaxial with the axis of rotation of the screwing means, projecting from the internal face of one of the two screwing end pieces to which it is connected, by one of its faces at least, substantially in the vicinity of half of the length of said end piece as well as by a sleeve of conjugate dimensions adapted for cooperating with said lip, formed on the other end piece.

In a first embodiment, said annular lip is provided between two cylindrical surfaces of the end piece to which it is connected, whereas in a second embodiment, said end piece has a conical surface from its external orifice as far as the circular edge limiting the free end of said annular lip.

To facilitate use of the device of the invention, it is complementarily provided for the length of the sleeve, measured parallel to its axis, is different from that of a skirt which carries the threads of the screwing means.

These latter are chosen, in accordance with another feature of the invention, so that the threads of one end piece have a slight play with respect to the threads of the other end piece, with accordingly elimination of any risk of jamming and easier use.

In a particularly advantageous embodiment, the arrangement of the screw threads of the two end pieces is also chosen so that engagement of said threads only takes place after a slight off-load angle of rotation, which also contributes to correct positioning of the two end pieces with respect to each other.

According to another feature of the invention, the threads of one of the end pieces are provided with discontinuities, such as notches, regularily offset from the angular point of view and the other end piece has bosses with a shape and dimensions conjugate with said discontinuities between said two screw threads.

Thus an obstacle to jamming is provided, on the one hand, and, on the other, a non return safety means in the assembled condition of the end pieces.

For further facilitating positioning of the two end pieces with respect to each other, the invention also provides for fitting the threaded end piece integrally secured to the pocket with means facilitating gripping thereof, such as grooves or knurling disposed on the periphery of the end piece as well as projections which form reference means, which are preferably disposed in the diametrical plane which is that at the beginning of the screw threads of said end piece.

In such an embodiment, the end piece conjugate with the one having the reference means mentioned is also provided with reference means, which are disposed so that, after connection of the two end pieces together, the angle formed by the diametrical plane of the reference means of the first end piece and the diametrical plane of the reference means of the second end piece is a multiple of the angle of rotation of the two end pieces with respect to each other.

In a particularly preferred embodiment, the screwing means are of the "quarter of a turn" type, that is to say the coupling of the two elements together is obtained by a 90° rotation.

The invention also provides a pocket for collecting body fluids and/or waste more especially for colostomy, ileostomy, or urostomy, adapted for entering into the construction of a device such as defined above and comprising, about an opening which is formed in one of its walls, an end piece with threaded means projecting from the external face of said wall and integral therewith.

The invention also provides a cutaneous protector adapted to enter into the construction of such a device having, on a pad adapted to be fixed to the body of the user by means of a pressure sensitive means, a belt or any other similar means, an end piece having threaded means, projecting from the face of said shoe opposite that intended to come into contact with the body of the user with, on said end piece, means adapted for providing sealing of the mounting of the collecting pocket on the protector during screwing of the end pieces together.

BRIEF DESCRIPTION OF THE DRAWINGS

The invention will be better understood from the following description, given by way of example with reference to the accompanying drawings in which:

FIG. 1 is a schematical perspective view of the two elements forming a device of the invention in a first embodiment thereof;

FIG. 2 is a bottom view of an end piece of the device of the invention;

FIG. 3 is a plane view of the other end piece;

FIG. 4 is a partial evolute view of the thread means of the end piece shown in FIG. 2;

FIG. 5 is a section through line 5—5 of FIG. 4, on a larger scale;

FIG. 5A is a section through line 5A—5A of FIG. 4, on a larger scale,

FIG. 6 is a view similar to that of FIG. 4 but for the piece shown in FIG. 3;

FIG. 6A is a section through line 6A—6A of FIG. 6, on a larger scale;

DESCRIPTION OF THE PREFERRED EMBODIMENTS

Figure 7:
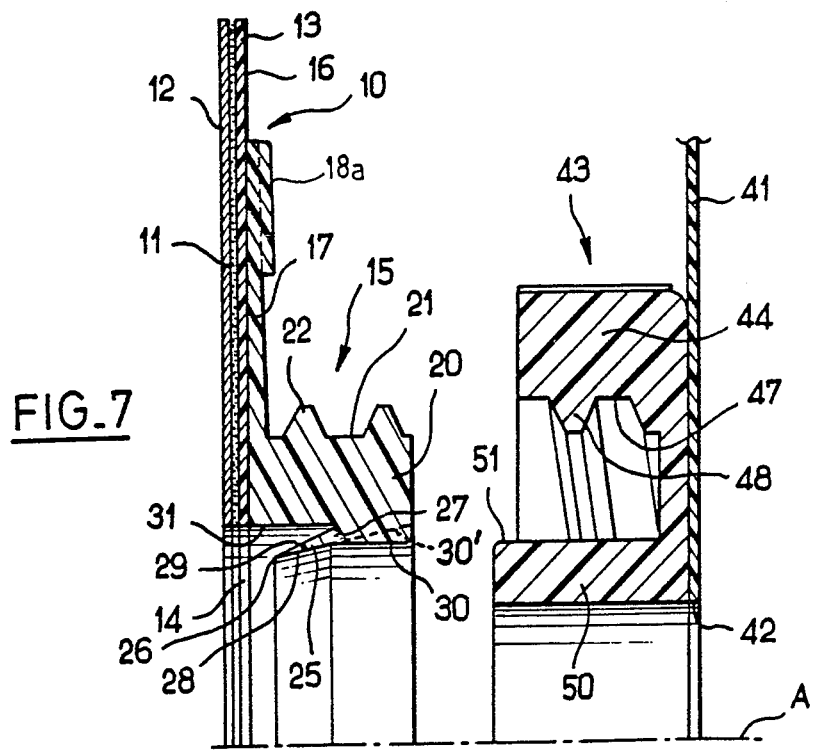
FIG. 7 is a partial view, on a larger scale and in section, of the device shown in FIG. 1.

Reference is made first of all to FIGS. 1 to 7 relative to a first embodiment of an improved ostomy device of the invention. It includes an element 10, provided for fixing about an artificial opening in the body of the user by means of a belt C or a similar means or, in a variant, by means of a lining 11 made from a pressure sensitive adhesive material, known per se, and which is generally protected, as long as the device is not used, by a film 12 which may be readily peeled away, FIG. 7.

Whatever its mode of fixing to the body of the user, element 10 includes essentially a pad or shoe 13 made from a flexible material, for example of a round, rectangular or polygonal shape intended to form a cutaneous protector of the peristomial zone about which it is placed and held, with its opening 14 concentric or substantially concentric to the stoma, and an end piece 15 firmly fixed to shoe 13, projecting from the face 16 of the shoe opposite the one carrying the adhesive material 11 or when such a material is not present, opposite that in contact with the skin of the user. In the embodiment described and shown, end piece 15 includes a base 17, of a generally circular shape with, however, in diametrically opposite zones, slight protuberances 18 and 19 which have slight radial thickened portions 18a and 19a respectively. End piece 15 also includes, integrally molded with said base 17 for example during manufacture by molding of a plastic material, a skirt 20 having on its external surface 21, screw threads 22, FIGS. 6 and 6A and, on its internal surface, a resilient deformable lip 25. This latter has a triangular cross section, connected to the body of skirt 20 by a base 27 (substantially at mid length of skirt 20) with faces 28 and 29 slanting with respect to said axis and which intersect at an angle of low value so as to define a circular ridge 26; the diameter of this latter is slightly less than that of a first cylindrical surface 30, with axis A, which is connected to base 27 which is also connected to a second cylindrical surface 31, with axis A, and of a diameter slightly greater than that of the surface 30.

In a variant, and as shown with broken lines in FIG. 7, the face 28 of the lip is connected to a conical surface 30' whose angle at the apex is at most equal to that defining face 28 and in its extension, so that the internal surface of skirt 20 between its input end and ridge 26 of the lip is conical.

In the embodiment shown of a "quarter of a turn" device, the discontinuous screw threads 22 of end piece 15 are four in number, offset by 90° with respect to each other, four bosses 22a evenly disposed from the angular point of view being provided between two contiguous threads, FIGS. 6 and 6A. The end piece is fixed to shoe 30 by welding, for example of the thermal or high frequency type or else by bonding by means of films compatible with the material forming end piece 15 and which are provided on face 16 of the shoe.

This latter may be formed from a hydrophilic adhesive mass of a thickness between 0.5 and 3 mm, or from a very thin acrylic adhesive mass whose thickness is between a few microns and about 200 microns or else by combining these two elements, that is to say by providing about the stoma a hydrophilic adhesive gum and, at the periphery thereof, an acrylic adhesive mass.

End piece 15 may be formed by molding high or low density polyethylene, or ethylene and vinyl acetate polymer (EVA) or polyvinyl chloride (PVC) or a polyamide and the compatible films for fixing the end piece on the cutaneous protector are then advantageously polyethylene, PVC, polyamide films or complex barrier films or non woven films having a polyester, polypropylene and/or polyethylene basis.

With element 10 of the ostomy device of the invention there cooperates, removably, a pocket 40, shown in FIG. 1, for collecting body fluids and/or waste discharged through the end piece 15, and which includes a wall 41, FIG. 7, pierced with a hole 42 through which the body fluids or waste penetrate inside the pocket, which may be of the disposable type or of the type to be emptied, depending on the requirements of practice. It may be made from a film of polyethylene, PVC or polyamide (such as the one known under the registered trademark RILSAN) or it may be a complex barrier film of the polyethylene/EVA/polyvinylidene chloride/EVA/polyethylene type, such as those known under the registered trademark SARANEX belonging to the firm DOW CHEMICAL, or a complex film of the EVA/polyvinylidene chloride and EVA type, such as those known under the trademark CRYOVA of the firm GRACE and under the registered trademark SARANEX of the firm DOW CHEMICAL, or else a complex film of the EVA/EVOH/EVA type or from rubber or similar. In accordance with the invention, with pocket 40 is associated an end piece 43, FIGS. 2, 4, 4A, 5 and 7, advantageously made from the same plastic material as end piece 15 for example from high density polyethylene and sealingly fixed to pocket 40, to which it is welded or bonded, as mentioned above, so that its axis is coaxial with that of the opening 42.

In the embodiment described and shown, end piece 43 has an external skirt 44, with generally circular flat contour (FIG. 2) with slight projections 46 evenly spaced apart at the periphery of said skirt at 90° from each other so as to serve as references, the external surface of the skirt being grooved or knurled between said projections as shown schematically at 45. The internal face 47 of skirt 44 has, integrally molded therewith, discontinuous screw threads 48, conjugate with threads 22 of end piece 15 and which, in the embodiment shown, are four in number, FIG. 4, evenly offset by 90° with respect to each other with, on said threads, notches 48a, FIG. 5A, of shape and dimensions conjugate with those of bosses 22a.

End piece 43 also has, integrally molded with skirt 44, a cylindrical sleeve 50 whose length, measured parallel to axis A, is greater than that of skirt 44 and in which the diameter of the external face 51 is less than the diameter of part 30 but slightly greater than that of ridge 26 so that said sleeve is adapted to resiliently deform lip 25 with which it engages when end piece 43 is screwed onto end piece 50 for sealingly fixing pocket 40 to the element 10 with cutaneous protector 13.

By forming the threads 48 of end piece 43 so that they have a slight play with respect to the threads 22 of end piece 15, on the one hand, by giving to the inlet of these threads a rounded section, as shown at 52 in FIG. 5, and by also providing, on the other hand, an arrangement of the threads such that their engagement only takes place after a slight empty angle of rotation, any risk of jamming is eliminated not only in positioning but also in removing the collecting pocket 40, which makes the device very easy to use not only in the case of colostomy, ileostomy, but also urostomy. The presence on one and the other of end pieces 15 and 43 of references formed by and on the protuberances 18 and 19 of end piece 15 and the projections 46 of end piece 43 also provided with grooving or knurling 45 facilitating tripping thereof contributes to the facility of use of the device. Notches 48a and bosses 22a advantageously oppose jamming of the two end pieces with respect to each other while forming non return safety catches which prevent untimely separation during use of the device.

Figure 8:
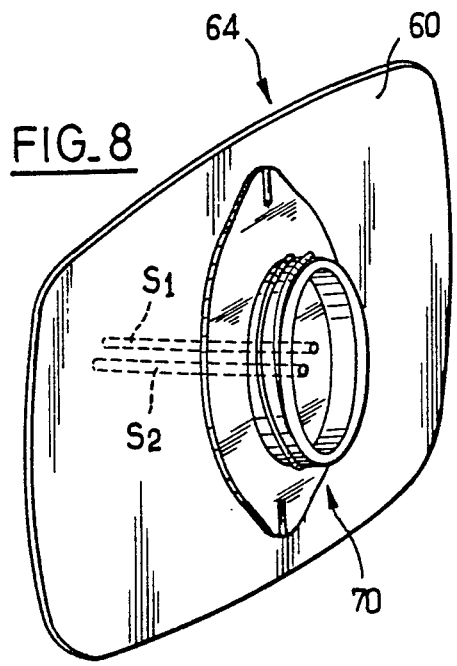
FIG. 8 is a schematical perspective view of one of the elements of another embodiment of the device of the invention.
Figure 9:
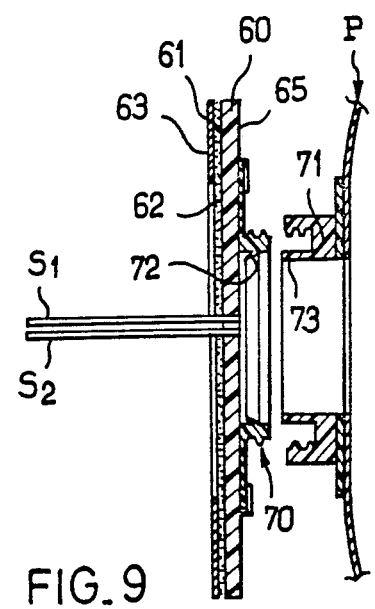
FIG. 9 is a sectional view of a device of the invention including the element shown in FIG. 8.

Reference will now be made to FIGS. 8 and 9 relative to another embodiment of a device of the invention, more particularly provided for collecting urine, for example for ureterostomized patients. Device 62 includes a cutaneous protector 60 one face 61 of which has a lining made of a pressure sensitive piece of material, advantageously protected by a film 63 as long as the device is not used and, integrally secured to this protection 60, one or two probes S1 and S2 intended to be introduced into a ureter stoma for the treatment of single or double urostomy.

In accordance with the invention, element 64 having the cutaneous protector 60 and the probe or probes S has projecting from its face 65—opposite face 61—an end piece 70 shown schematically in FIGS. 8 and 9 and whose structure is similar, if not identical, to that of end piece 15 of the preceding embodiment, said end piece being provided for sealingly mounting a collecting pocket P, FIG. 9, having an end piece 71 of similar or identical structure to that of end piece 43 of the preceding embodiment. In this embodiment it is also through a lip 72 formed on the inner face of the tubular end piece 70 and with which a sleeve 73 is adapted to cooperate having a shape and dimensions conjugate with end piece 71, that sealing is provided.

End piece 70 is fixed to the cutaneous protector 60 by a thermal or high frequency welding, or by bonding, as is mentioned above, advantageously with use of compatible films between the end piece and the cutaneous protector and end piece 71 is fixed to pocket P by a similar welding or bonding process.

Good results have been obtained with a device such as shown in FIG. 1 having a SARANEX (registered trademark of DOW CHEMICAL) collecting pocket and formed by molding high density polythene in which end piece 15 had an external diameter of about 75 mm, a length measured parallel to axis A of about 5 mm, a diameter of the cylindrical part 30 of 54.5 mm, a diameter of part 31 of 56 mm and a diameter of lip 26 of 53.5 mm, whereas the external diameter of sleeve 50 was 54 mm and its internal diameter 50 mm, the external diameter of end piece 43 being about 70 mm for four right hand threads with a pitch of ten.

What is claimed is:

1. An ostomy device having
   a first element adapted to be removably fixed about an artificial opening of the body by means of a pressure sensitive adhesive means, a belt or other similar means and comprising a pad forming a cutaneous protector of the peristomial zone, having a first opening having an axis;
   a second element including a collecting pocket for collecting fluids and/or waste, removably coupled to said first element, said second element having a second opening;
   a first screwing end piece fixed to said pad within said first opening and having an internal and an external surface, an outer thread on said external surface and an annular resiliently deformable lip coaxial with said axis having a first free end, said lip projecting from said internal surface, and wherein said internal surface of said first end piece has a second free end and a ridge limiting said first free end of said lip, and said internal surface of said first end piece comprises a conical portion extending from said second free piece comprises a conical portion extending from said second free end to said ridge; and a second screwing end piece adapted to cooperate with said first end piece, fixed to said collecting pocket within said second opening, having a skirt carrying an inner thread fitted to cooperate with said outer thread of said first end piece, and a sleeve of conjugate dimensions adapted to cooperate with said lip, coaxial with said internal thread.

2. The device as claimed in claim 1, wherein said free end of the lip has a triangular cross section slanted with respect to said axis, said lip being connected to said internal surface over a length of about half the length of said internal surface.

3. The device as claimed in claim 2, wherein said internal surface of said first end piece has two cylindrical surfaces and said lip is connected to said end piece between said surfaces.

4. The device as claimed in claim 2, wherein said sleeve is longer than said skirt.

5. The device as claimed in claim 1, wherein said inner and outer threads have a slight play with respect to each other.

6. The device as claimed in claim 1, wherein said inner and outer threads engage with respect to each other only after a slight off load angle of rotation.

7. The ostomy device as claimed in claim 1, more especially for colostomy, ileostomy, or urostomy, wherein said collecting pocket comprises walls having inner and outer respective surfaces, carrying said second opening and said second end piece, wherein said second end piece is integral with one of said walls and projects from the external surface of said one of said walls.

8. The ostomy device as claimed in claim 1, wherein said first element comprises a cutaneous protector device including a shoe building up said pad adapted to be fixed to the body of the user by means of a pressure sensitive adhesive or belt or any other similar means, said shoe having a first face intended to come into contact with the body of the user, and a second face, opposite to said first face, said first end piece projecting from said second face.

9. The device as claimed in claim 8 including at least one probe adapted to be introduced into at least one ureta stoma and integral with at least one of said shoe and said first end piece.

10. An ostomy device having a first element adapted to be removably fixed about an artificial opening of the body by means of a pressure sensitive adhesive means, a belt or other similar means and comprising a pad forming a cutaneous protector of the peristomial zone, having a first opening having an axis;

a second element including a collecting pocket for collecting fluids and/or waste, removably coupled to said first element, said second element having a second opening;

a first screwing end piece fixed to said pad within said first opening and having an internal and an external surface, an outer thread on said external surface and an annular resiliently deformable lip coaxial with said axis having a first free end, said lip projecting from said internal surface;

a second screwing end piece adapted to cooperate with said first end piece, fixed to said collecting pocket within said second opening, having a skirt carrying an inner thread fitted to cooperate with said outer thread of said first end piece, and a sleeve of conjugate dimensions adapted to cooperate with said lip, coaxial with said internal thread; and notches provided on the threads of one of said first and second end pieces and bosses with shape and dimensions matching with said notches, provided between said threads of the other one of said end pieces.

11. An ostomy device having a first element adapted to be removably fixed about an artificial opening of the body by means of a pressure sensitive adhesive means, a belt or other similar means and comprising a pad forming a cutaneous protector of the peristomial zone, having a first opening having an axis;

a second element including a collecting pocket for collecting fluids and/or waste, removably coupled to said first element, said second element having a second opening;

a first screwing end piece fixed to said pad within said first opening and having an internal and an external surface, an outer thread on said external surface and an annular resiliently deformable lip coaxial with said axis having a first free end, said lip projecting from said internal surface;

a second screwing end piece adapted to cooperate with said first end piece, fixed to said collecting pocket within said second opening, having a skirt carrying an inner thread fitted to cooperate with said outer thread of said first end piece, and a sleeve of conjugate dimensions adapted to cooperate with said lip, coaxial with said internal thread; and gripping means, such as grooves or knurling disposed on the periphery of said second end piece, and reference means such as projections on said second end piece, disposed in the diametral plane of the beginning of the threads of said second end piece.

12. An ostomy device having a first element adapted to be removably fixed about an artificial opening of the body by means of a pressure sensitive adhesive means, a belt or other similar means and comprising a pad forming a cutaneous protector of the peristomial zone, having a first opening having an axis;

a second element including a collecting pocket for collecting fluids and/or waste, removably coupled to said first element, said second element having a second opening;

a first screwing end piece fixed to said pad within said first opening and having an internal and an external surface, an outer thread on said external surface and an annular resiliently deformable lip coaxial with said axis having a first free end, said lip projecting from said internal surface;

a second screwing end piece adapted to cooperate with said first end piece, fixed to said collecting pocket within said second opening, having a skirt carrying an inner thread fitted to cooperate with said outer thread of said first end piece, and a sleeve of conjugate dimensions adapted to cooperate with said lip, coaxial with said internal thread; and wherein said inner and outer threads form screwing means of the quarter of turn type.

* * * * *